US008323316B2

(12) United States Patent  (10) Patent No.: US 8,323,316 B2
Maiorino et al.  (45) Date of Patent: Dec. 4, 2012

(54) KNOTTED SUTURE END EFFECTOR

(75) Inventors: Nicholas Maiorino, Branford, CT (US); Ahmad Robert Hadba, Middlefield, CT (US); Gerald Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 271 days.

(21) Appl. No.: 12/729,846

(22) Filed: Mar. 23, 2010

(65) Prior Publication Data

US 2010/0204730 A1  Aug. 12, 2010

Related U.S. Application Data

(63) Continuation-in-part of application No. 12/571,806, filed on Oct. 1, 2009.

(60) Provisional application No. 61/104,085, filed on Oct. 9, 2008.

(51) Int. Cl.
*A61B 17/04* (2006.01)
*A61L 17/00* (2006.01)

(52) U.S. Cl. ........................ 606/232; 606/228
(58) Field of Classification Search .................. 606/139, 606/228–232; 528/272; 523/105
See application file for complete search history.

(56) References Cited

U.S. PATENT DOCUMENTS

| | | | |
|---|---|---|---|
| 3,580,256 A | 5/1971 | Wilkinson | |
| 3,664,345 A | 5/1972 | Dabbs et al. | |
| 3,729,008 A | 4/1973 | Berkovits | |
| 3,890,977 A | 6/1975 | Wilson | |
| 4,321,002 A | 3/1982 | Froehlich | |
| 4,669,473 A | 6/1987 | Richards et al. | |
| 4,719,917 A | 1/1988 | Barrows et al. | |
| 4,738,666 A | 4/1988 | Fuqua | |
| 4,741,330 A | 5/1988 | Hayhurst | |
| 4,898,156 A | 2/1990 | Gatturna et al. | |
| 4,901,721 A | 2/1990 | Hakki | |
| 4,950,285 A | 8/1990 | Wilk | |
| 5,041,129 A | 8/1991 | Hayhurst et al. | |
| 5,071,429 A | 12/1991 | Pinchuk et al. | |
| 5,178,629 A | 1/1993 | Kammerer | |
| 5,258,000 A | 11/1993 | Gianturco | |
| 5,279,564 A | 1/1994 | Taylor | |
| 5,312,436 A | 5/1994 | Coffey et al. | |
| 5,415,635 A | 5/1995 | Bagaoisan et al. | |
| 5,423,858 A | 6/1995 | Bolanos et al. | |
| 5,464,425 A | 11/1995 | Skiba | |

(Continued)

FOREIGN PATENT DOCUMENTS

DE  2900265 A1  7/1980

(Continued)

OTHER PUBLICATIONS

European Search Report for EP 09252392.7-2310 date of completion is Feb. 15, 2010 (3 pages).

(Continued)

*Primary Examiner* — Julian Woo

(57) ABSTRACT

A suture including a knotted end effector is provided. The suture includes a body portion defining a longitudinal axis and an end effector formed from the body portion. The end effector includes first and second extensions which extend outwardly from the longitudinal axis in opposite directions when the end effector is in a permanent configuration. The extensions of the end effector extend substantially along the longitudinal axis when the end effector is in a temporary position. In embodiments, at least a portion of the end effector includes a shape memory material.

27 Claims, 13 Drawing Sheets

U.S. PATENT DOCUMENTS

| | | | |
|---|---|---|---|
| 5,468,248 A | 11/1995 | Chin et al. | |
| 5,573,286 A | 11/1996 | Rogozinski | |
| 5,628,756 A | 5/1997 | Barker, Jr. et al. | |
| 5,728,109 A * | 3/1998 | Schulze et al. | 606/139 |
| 5,769,862 A | 6/1998 | Kammerer et al. | |
| 5,865,836 A | 2/1999 | Miller | |
| 5,968,069 A | 10/1999 | Dusbabek et al. | |
| 6,132,438 A * | 10/2000 | Fleischman et al. | 606/139 |
| 6,159,139 A | 12/2000 | Chiu | |
| 6,160,084 A * | 12/2000 | Langer et al. | 528/272 |
| 6,171,299 B1 | 1/2001 | Bonutti | |
| 6,235,869 B1 | 5/2001 | Roby et al. | |
| 6,281,262 B1 * | 8/2001 | Shikinami | 523/105 |
| 6,358,266 B1 | 3/2002 | Bonutti | |
| 6,388,043 B1 | 5/2002 | Langer et al. | |
| 6,524,283 B1 | 2/2003 | Hopper et al. | |
| 6,551,282 B1 | 4/2003 | Exline et al. | |
| 6,589,208 B2 | 7/2003 | Ewers et al. | |
| 6,596,014 B2 | 7/2003 | Levinson et al. | |
| 6,596,015 B1 * | 7/2003 | Pitt et al. | 606/232 |
| 6,626,916 B1 | 9/2003 | Yeung | |
| 6,626,919 B1 | 9/2003 | Swanstrom | |
| 7,220,265 B2 * | 5/2007 | Chanduszko et al. | 606/139 |
| 7,341,571 B1 | 3/2008 | Harris et al. | |
| 8,118,834 B1 * | 2/2012 | Goraltchouk et al. | 606/228 |
| 2002/0095165 A1 | 7/2002 | Chan | |
| 2002/0095169 A1 | 7/2002 | Maitland et al. | |
| 2002/0165561 A1 | 11/2002 | Ainsworth et al. | |
| 2003/0149447 A1 | 8/2003 | Morency et al. | |
| 2003/0236445 A1 | 12/2003 | Couvillon | |
| 2003/0236531 A1 | 12/2003 | Couvillon | |
| 2003/0236533 A1 | 12/2003 | Wilson et al. | |
| 2003/0236534 A1 | 12/2003 | Kayan | |
| 2004/0138702 A1 | 7/2004 | Peartree et al. | |
| 2004/0204723 A1 | 10/2004 | Kayan | |
| 2004/0260343 A1 | 12/2004 | Leclair | |
| 2005/0082826 A1 | 4/2005 | Werth | |
| 2005/0149062 A1 | 7/2005 | Carroll | |
| 2005/0171562 A1 | 8/2005 | Criscuolo et al. | |
| 2005/0267531 A1 | 12/2005 | Ruff et al. | |
| 2005/0273138 A1 | 12/2005 | To et al. | |
| 2006/0116718 A1 | 6/2006 | Leiboff | |
| 2006/0229675 A1 | 10/2006 | Novoa et al. | |
| 2007/0038238 A1 | 2/2007 | Freeman et al. | |
| 2007/0106319 A1 | 5/2007 | Au et al. | |
| 2007/0203511 A1 | 8/2007 | Vardi | |
| 2007/0203517 A1 | 8/2007 | Williams et al. | |
| 2007/0208276 A1 | 9/2007 | Kornkven Volk | |
| 2007/0225651 A1 | 9/2007 | Rosenberg et al. | |
| 2008/0015598 A1 | 1/2008 | Prommersberger | |
| 2008/0294193 A1 | 11/2008 | Schwartz et al. | |
| 2009/0105655 A1 | 4/2009 | DeSantis et al. | |
| 2009/0105659 A1 | 4/2009 | Bettuchi et al. | |
| 2009/0105691 A1 | 4/2009 | Sung | |

FOREIGN PATENT DOCUMENTS

| | | |
|---|---|---|
| EP | 1747759 | 1/2007 |
| EP | 1747772 | 1/2007 |
| EP | 1878391 | 1/2008 |
| EP | 1946705 A2 | 7/2008 |
| EP | 2050404 | 4/2009 |
| EP | 2050405 | 4/2009 |
| EP | 2050406 | 4/2009 |
| WO | WO 00/57796 A1 | 10/2000 |
| WO | WO 02/00286 | 1/2002 |
| WO | WO 02/094106 A1 | 11/2002 |
| WO | WO 03/088818 A2 | 10/2003 |
| WO | WO 2004/004577 A1 | 1/2004 |
| WO | WO 2004/052594 | 6/2004 |
| WO | WO 2004/060463 | 7/2004 |
| WO | WO 2004/105621 | 12/2004 |
| WO | WO 2005/000001 | 1/2005 |
| WO | WO2006111394 A2 | 10/2006 |
| WO | WO 2007/038715 | 4/2007 |
| WO | WO 2009/087105 A1 | 7/2009 |

OTHER PUBLICATIONS

European Search Report for EP 11250356.0-1269 date of completion is Jun. 20, 2011 (3 pages).

Lendlein, et al., "Shape-memory polymers as stimuli-sensitive implant materials", *Clinical Hemorheology and Microcirculation* 2005, 32:105-116.

Lendlein, et al., "Biodegradable, Elastic Shape-Memory Polymers for Potential Biomedical Applications", *Science* 2002, 296:1673-1676.

Lendlein, "Solving a knotty problem—surgical sutures from shape memorypolymers", *Materials World* 2002, 10(7):29-30.

Small, et al., "Laser-activated shape memory polymer intravascular thrombectomy device", *Optics Express* 2005, 13(20):8204-8213.

Faré, et al., "In vitro interaction of human fibroblasts and platelets with a shape-memory polyurethane", *Fibroblast/Platelet Interaction With SMPu* Wiley Periodicals, Inc. (2005), pp. 1-11.

Tim Thompson, "Polyurethanes as Specialty Chemicals Principles and Applications", 2005 CRC Press, Chapter 2: Polyurethane Chemistry in Brief.

Annex to European Search Report in European Application No. EP10 25 1485 dated Dec. 6, 2010.

* cited by examiner

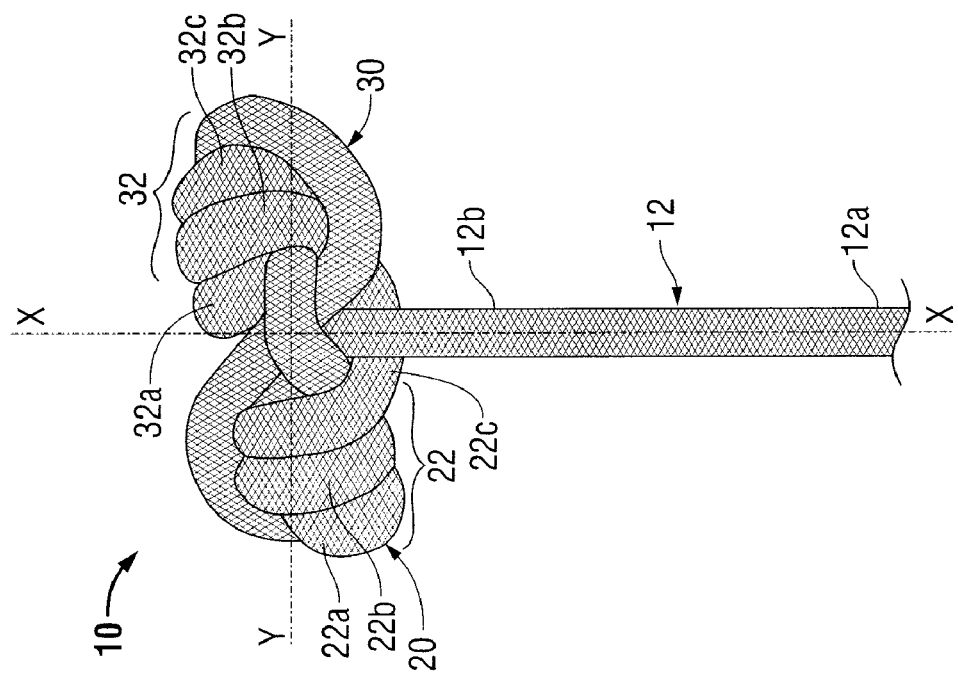
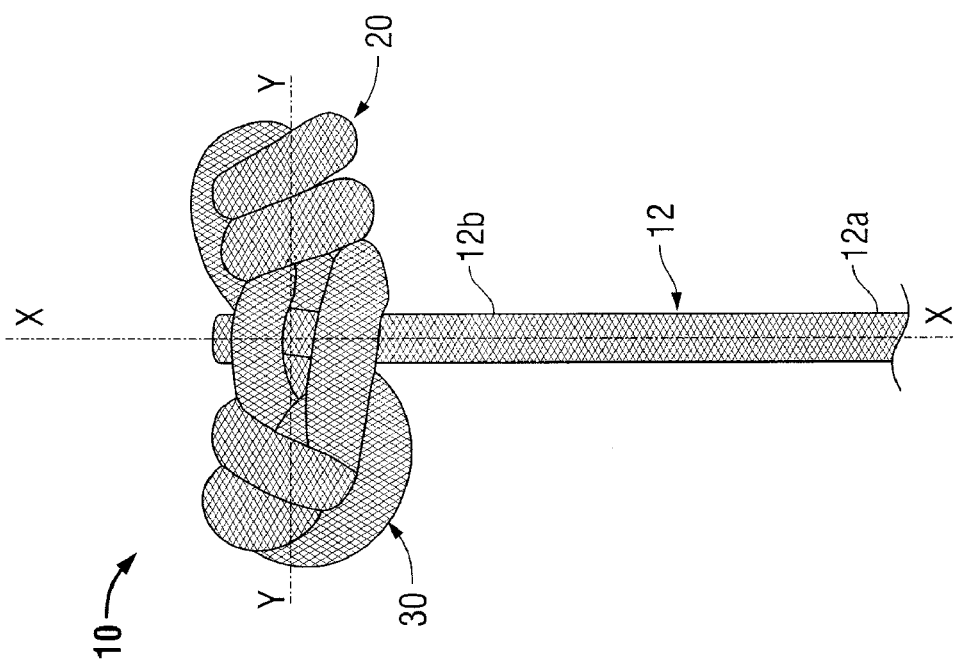

KNOTTED SUTURE END EFFECTOR

CROSS-REFERENCE TO RELATED APPLICATIONS

The present application is a continuation-in-part of U.S. patent application Ser. No. 12/571,806, filed Oct. 1, 2009, which claims benefit of and priority to U.S. Provisional Application No. 61/104,085, filed Oct. 9, 2008, the entire disclosures of each of which are incorporated by reference herein.

BACKGROUND

1. Technical Field

The present disclosure relates to sutures for use in medical procedures. More particularly, the present disclosure relates to a knotted end effector for a suture.

2. Background of Related Art

Medical sutures may be formed from a variety of materials and may be configured for use in limitless applications. The proximal end of the suture may have a sharpened tip or may include a needle for penetrating tissue. A distal end of the suture may include an anchor or end effector for maintaining the suture in engagement with the tissue as the suture is pulled through the tissue. End effectors are available in many size and configurations. Typically, an end effector is formed independently of the suture and is later attached to the distal end of the suture.

In many instances, a clinician may prefer to tie a knot in the suture to anchor the suture within the tissue. Although the clinician may find this practice convenient, the knot formed on the end of the tissue is not always suitable to prevent the suture from being pulled through the tissue, for example, when the knot slips or is too small to engage the tissue. Additionally, the tying of a knot, especially with the fine suture material required for use in many procedures, is tedious and time consuming.

Therefore, a continuing need exists for a knotted end effector and a method of making a knotted end effector.

SUMMARY

A suture have an end effector is provided. The suture includes a body portion defining a longitudinal axis and an end effector formed from the body portion. The end effector includes a shape memory material. The end effector includes first and second extensions extending outwardly from the longitudinal axis in opposite directions when the end effector is in a permanent configuration. The extensions of the end effector extend substantially along the longitudinal axis when the end effector is in a temporary position.

In embodiments, the end effector is integrally formed with the body portion. The end effector may be substantially perpendicular to the longitudinal axis when in the permanent configuration. The end effector may define a substantially T-shape when the end effector is in the permanent configuration and may be substantially parallel to the longitudinal axis when the end effector is in the temporary configuration. Alternatively, the end effector may define a substantially Y-shape when the end effector is in the temporary configuration. The first and second extensions may include a plurality of throws. The shape memory polymer may be degradable materials, non-degradable materials, and combinations thereof.

Also provided is a suture having an end effector including shape memory features. The suture includes a body portion defining a longitudinal axis and an end effector integrally formed from the body portion. The end effector may include a shape memory material and may include first and second extensions extending substantially along the longitudinal axis when the end effector is in a permanent configuration. The extensions of the end effector may extend outwardly from the longitudinal axis in opposite directions when the end effector is in a temporary position.

Additionally, a suture including an end effector is provided. The suture includes a body portion defining a longitudinal axis and an end effector including a shape memory material integrally formed from the body portion. The end effector may include first and second extensions extending outwardly from the longitudinal axis in opposite directions. Either or both of the first and second extensions may become rigid upon transitioning of the end effector from a temporary configuration to a permanent configuration.

In other embodiments, a suture includes a body portion defining a longitudinal axis and an end effector comprising a shape memory material integrally formed from the body portion. The end effector may include first and second extensions extending outwardly from the longitudinal axis in opposite directions. Either or both of the first and second extensions may become slack upon transitioning of the end effector from a temporary configuration to a permanent configuration.

Further still, a suture includes a body portion defining a longitudinal axis. The body portion includes a distal portion and a proximal portion. The distal portion includes an end effector and the proximal portion includes a needle. The end effector includes a shape memory material. When the end effector is in a permanent configuration, the end effector limits movement of the distal portion of the suture through tissue.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a back view of an end effector according to an embodiment of the present disclosure;

FIG. 2 is a front view of the end effector of FIG. 1;

DETAILED DESCRIPTION

Figure 3A:
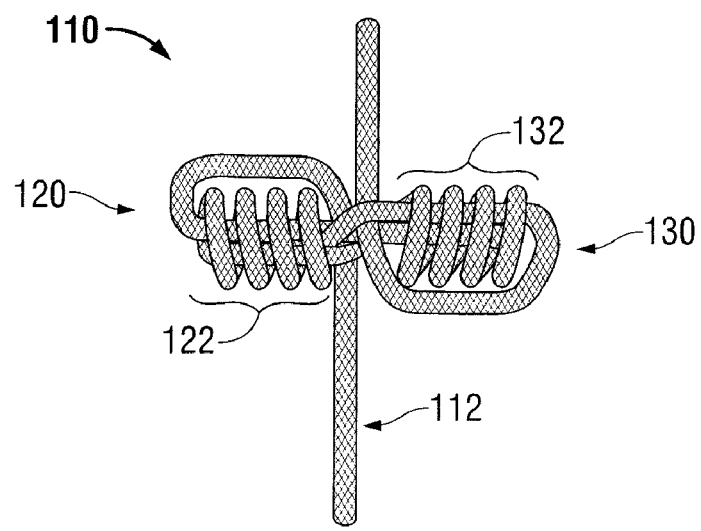
FIGS. 3A and 3B are front views of an alternate embodiment of the present disclosure in first configuration (FIG. 3A) and in a second configuration (FIG. 3B)

Referring initially to FIGS. 1 and 2, an embodiment of an end effector according to the present disclosure is shown generally as end effector 10. Although, as shown, end effector 10 is formed on a distal end 12b of suture 12, end effector 10 may be formed anywhere along the length of suture 12.

Suture 12 may be formed of any material within the purview of those skilled in the art, such as, for example, degradable materials, non-degradable materials, natural materials, synthetic materials, shape memory materials, metals, alloys, and combinations thereof. More particularly, suture 12 may be formed of a degradable material selected from the group consisting of polyesters, polyorthoesters, polymer drugs, polyhydroxybutyrates, lactones, proteins, cat gut, collagens, carbonates, homopolymers thereof, copolymers thereof, and combinations thereof. In other embodiments, suitable degradable materials which may be utilized to form suture 12 include natural collagenous materials or synthetic resins including those derived from alkylene carbonates such as trimethylene carbonate, tetramethylene carbonate, and the like; caprolactone; dioxanone; glycolic acid; lactic acid; homopolymers thereof; copolymers thereof; and combinations thereof. In some embodiments, glycolide and lactide based polyesters, especially copolymers of glycolide and lactide, may be utilized to form suture 12.

In yet other embodiments, suitable materials for forming suture 12 include homopolymers, copolymers, and/or blends possessing glycolic acid, lactic acid, glycolide, lactide, dioxanone, trimethylene caprolactone, and various combinations of the foregoing. For example, in some embodiments, a copolymer of glycolide and trimethylene carbonate is used to form suture 12. Methods for forming such copolymers are within the purview of those skilled in the art and include, for example, the methods disclosed in U.S. Pat. Nos. 4,300,565 and 5,324,307, the entire disclosures of each or which are incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments, from about 30% to about 35% by weight of the copolymer.

Other suitable materials for forming suture 12 include copolymers of lactide and glycolide, with lactide present in an amount from about 6% to about 12% by weight of the copolymer and glycolide being present in amounts from about 88% to about 94% by weight of the copolymer. In some embodiments, lactide is present from about 7% to about 11% by weight of the copolymer with glycolide being present in amounts from about 89% to about 98% by weight of the copolymer. In some other embodiments, lactide is present in an amount of about 9% by weight of the copolymer with the glycolide being present in an amount of about 91% by weight of the copolymer.

In some embodiments, suitable materials for forming suture 12 include copolymers of glycolide, dioxanone, and trimethylene carbonate. Such materials may include, for example, copolymers possessing glycolide in amounts from about 55% to about 65% by weight of the copolymer, in embodiments, from about 58% to about 62% by weight of the copolymer, in some embodiments, about 60% by weight of the copolymer; dioxanone in amounts from about 10% to about 18% by weight of the copolymer, in embodiments, from about 12% to about 16% by weight of the copolymer, in some embodiments about 14% by weight of the copolymer; and trimethylene carbonate in amounts from about 17% to about 35% by weight of the copolymer, in embodiments, from about 22% to about 30% by weight of the copolymer, in some embodiments, about 26% by weight of the copolymer.

Other suitable materials for forming suture 12 include a copolymer of glycolide, lactide, trimethylene carbonate, and ε-caprolactone. Such materials may include, for example, a random copolymer possessing caprolactone in amounts from about 14% to about 20% by weight of the copolymer, in embodiments, from about 16% to about 18% by weight of the copolymer, in some embodiments, about 17% by weight of the copolymer; lactide in amounts from about 4% to about 10% by weight of the copolymer, in embodiments, from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in some embodiments about 7% by weight of the copolymer; and glycolide in amounts from about 60% to about 78% by weight of the copolymer, in embodiments, from about 66% to about 72% by weight of the copolymer, in some embodiments about 69% by weight of the copolymer.

Suitable non-degradable materials which may be utilized to form suture 12 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. Other suitable non-degradable materials include silk, cotton, linen, carbon fibers, and the like. The polypropylene may be isotactic polypropylene or a mixture of isotactic and syndiotactic or atactic polypropylene.

Suture 12 may be formed using any technique within the purview of those skilled in the art, such as, for example, extrusion, molding and/or gel spinning. In some embodiments, suture 12 may include a yarn made of more than one filament, which may contain multiple filaments of the same or different materials. Where suture 12 is made of multiple filaments, suture 12 may be made using any known technique such as, for example, braiding, weaving or knitting. Suture 12 may also be combined to produce a non-woven suture. Suture 12 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

In some embodiments, suture 12 may be formed of a shape memory polymeric material. Shape memory polymeric materials possess a permanent shape and a temporary shape. Commonly, the temporary shape is of a configuration which enhances the ability of a surgeon to introduce suture 12 into a patient's body. The permanent shape, which is assumed in vivo upon application of energy, such as heat or light, is of a configuration which enhances the retention of suture 12 in tissue.

Shape memory polymers are a class of polymers that, when formed into an object such as suture 12, can be temporarily deformed by mechanical force and then caused to revert back to an original shape when stimulated by energy. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

In the case of heat stimulated shape memory polymers, a transition temperature ($T_{Trans}$) exists at which the shape change occurs during heating. The shape memory polymers can thus be tailored by altering material properties at the molecular level and by varying processing parameters. An object's primary shape may be formed with heat and pressure at a temperature at which the soft domains are flexible and the hard domains are not fully formed. The object may then be cooled so that the hard domains are more fully formed and the soft domains become rigid. The secondary or temporary shape can be formed by mechanically deforming the object, which is most readily accomplished at a temperature approaching or above $T_{Trans}$. Mechanical stresses introduced into the object are then locked into place by cooling the object to temperatures below $T_{Trans}$, so that the soft segments solidify to a rigid state. Once the object is heated to $T>T_{Trans}$, the soft segments soften and relax back to their original configuration and the object returns to its primary or original shape, sometimes referred to herein, as its permanent shape. The temperature at which a shape memory material reverts to its permanent shape may be referred to, in embodiments, as its permanent temperature ($T_{perm}$).

Polymers possessing shape memory properties which may be used to construct suture 12 include, for example, synthetic materials, natural materials (e.g., biological) and combinations thereof, which may be biodegradable and/or non-biodegradable. As used herein, the term "biodegradable" includes both bioabsorbable and bioresorbable materials. By "biodegradable", it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Suitable non-degradable materials that may be used to form suture 12 include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other.

Suitable bioabsorbable polymers for forming suture 12 include, but are not limited to, aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as poly(bisphenol A-iminocarbonate and the like); polyorthoesters; polyoxaesters including those containing amine groups; polyphosphazenes; poly(propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

Suitable aliphatic polyesters may include, but are not limited to, homopolymers and copolymers of lactide (including lactic acid, D-, L- and meso lactide); glycolide (including glycolic acid); epsilon-caprolactone; p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized to form suture 12. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In some embodiments, suture 12 may include combinations of both degradable and non-degradable materials. The degradable and/or non-degradable materials may have shape memory characteristics as described herein.

In other embodiments, the shape memory polymer forming suture 12 may be a copolymer of two components with different thermal characteristics, such as oligo (epsilon-caprolactone) dimethacrylates and butyl acrylates, including poly (epsilon-caprolactone)dimethacrylate-poly (n-butyl acrylate), or a diol ester and an ether-ester diol such as oligo (epsilon caprolactone) diol/oligo (p-dioxanone)diol copolymers. These multi-block oligo (epsilon-caprolactone) diol/oligo (p-dioxanone)diol copolymers possess two block segments: a "hard" segment and a "switching" segment linked together in linear chains. Such materials are disclosed, for example, in Lendlein, "Shape Memory Polymers-Biodegradable Sutures," Materials World, Vol. 10, no. 7, pp. 29-30 (July 2002), the entire disclosure of which is incorporated by reference herein.

In still other embodiments, suture 12 may be formed of blends of bioabsorbable materials including, but not limited to, urethanes blended with lactic acid and/or glycolic acid, homopolymers thereof or copolymers thereof, and acrylates blended with caprolactones such as polycaprolactone dimethacrylate poly(butyl acrylate) blends, and combinations thereof.

Other examples of suitable shape memory polymers and means for forming permanent and temporary shapes therewith are set forth in Lendlein et al., "Shape memory polymers as stimuli-sensitive implant materials," Clinical Hemorheology and Microcirculation, 32 (2005) 105-116, Lendlein et al., "Biodegradable, Elastic Shape memory Polymers for Potential Biomedical Applications," Science, Vol. 269 (2002) 1673-1676, and Lendlein et al., "Shape-Memory Polymers," Angew. Chem. Int. Ed., 41 (2002) 2035-2057, the entire disclosures of each of which are incorporated by reference herein.

Table 1 below further illustrates compositions which demonstrate shape memory effects and may be used to form suture 12. The block copolymers of each composition are in annealed wire format, the proposed soft and hard segments, and the glass transition temperature ($T_g$), having been measured by differential scanning calorimetry which is equal to $T_{Trans}$.

TABLE 1

| Composition (mol %) | Soft Domain | Hard Domain | $T_g$ ($T_{Trans}$) [° C.] |
|---|---|---|---|
| 15% Polydioxanone 85% Poly (L-lactide) | Polydioxanone and Amorphous Polylactide | Crystalline Polylactide | 54 |
| 20% Polydioxanone 80% Poly (L-lactide) | Polydioxanone and Amorphous Polylactide | Crystalline Polylactide | 45 |
| 15% Trimethylene Carbonate 85% Poly (L-lactide) | Trimethylene Carbonate and Amorphous Polylactide | Crystalline Polylactide | 54 |
| 20% Trimethylene Carbonate 80% Poly (L-lactide) | Trimethylene Carbonate and Amorphous Polylactide | Crystalline Polylactide | 55 |

The copolymers in Table 1 may undergo a partial shift when approaching $T_g$ and $T_{Trans}$ may be depressed when the materials are in aqueous solution. Since these polymers degrade by water absorption and bulk hydrolysis, water molecules entering the polymer matrices may act as plasticizers, causing the soft segments to soften at lower temperatures than in dry air. Thus, polymers exhibiting $T_{Trans}$ depression in aqueous solution may maintain a temporary shape through temperature excursions in the dry state, such as during shipping and storage, and shape shift to its permanent shape at body temperatures upon implantation.

Thus, in embodiments, the shape memory polymer may include a block copolymer of polydioxanone and polylactide with the polydioxanone present in an amount from about 5 mol % to about 20 mol % of the copolymer, in embodiments from about 15 mol % to about 19 mol % of the copolymer, and the polylactide present in an amount from about 80 mol % to about 95 mol % of the copolymer, in embodiments from about 81 mol % to about 85 mol % of the copolymer. In other embodiments, the shape memory polymer may include a block copolymer of trimethylene carbonate and polylactide, with the trimethylene carbonate present in an amount from about 5 mol % to about 20 mol % of the copolymer, in embodiments from about 15 mol % to about 19 mol % of the copolymer, and the polylactide may be present in an amount from about 80 mol % to about 95 mol % of the copolymer, in embodiments from about 81 mol % to about 85 mol % of the copolymer.

It is envisioned that $T_{Trans}$ may be tailored by changing block segment molar ratios, polymer molecular weight, and time allowed for hard segment formation. In embodiments, $T_{Trans}$ may be tailored by blending various amounts of low molecular weight oligomers of the soft segment domain into the copolymer. Such oligomers may segregate to soft domains and act as plasticizers to cause a downward shift in $T_{Trans}$.

Additionally, the copolymers forming suture 12 may include emulsifying agents, solubilizing agents, wetting agents, taste modifying agents, plasticizers, active agents, water soluble inert fillers, preservatives, buffering agents, coloring agents, and stabilizers. The addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums.

In some embodiments, crystalline degradable salts or minerals may be added to the block copolymer compositions to create polymer composites which may improve shape memory properties. An example of such a composite using polylactide homopolymer and crystalline hydroxyapatite is described in Zheng et al., "Shape memory properties of poly (D,L-lactide/hydroxyapatite composites," Biomaterials, 27 (2006) 4288-4295, the entire disclosure of which is incorporated by reference herein.

Other shape memory materials, including shape memory metals and metal alloys such as Nitinol, may also be used to form suture 12.

In embodiments, a molding process may be utilized to produce suture 12. Plastic molding methods are within the purview of those skilled in the art and include, but are not limited to, melt molding, solution molding, and the like. Injection molding, extrusion molding, compression molding and other methods can also be used as the melt molding technique. Once placed in the mold with the proper dimensions and configuration, the polymeric material used to form suture 12 may be heated to a suitable temperature, such as the permanent temperature ($T_{perm}$) which may, in embodiments, be the melting temperature of the shape memory polymeric material utilized to form the surgical end effector, i.e., suture 12 and/or end effector 10. Heating of suture 12 may be at suitable temperatures including, for example, from about 40° C. to about 180° C., in embodiments from about 80° C. to about 150° C., for a period of time of from about 2 minutes to about 60 minutes, in other embodiments from about 15 minutes to about 20 minutes, to obtain the permanent shape and dimensions.

The temperature for deformation treatment of suture 12 and/or end effector 10 molded with a previously memorized shape is one that makes possible ready deformation without producing cracks and should not exceed the temperature adopted for the shape memorization (e.g., $T_{perm}$). Deformation treatment at a temperature exceeding that for the original shape memorization may cause the object to memorize/program a new deformed shape. After suture 12 and/or end effector 10 with the desired shape has been formed, suture 12 and/or end effector 10 may be deformed above $T_{trans}$ to obtain an alternate, temporary configuration.

Suitable temperatures for deformation will vary depending on the shape memory polymer utilized, but generally may be above the transition temperature of the polymer ($T_{trans}$), but below the $T_{perm}$. In embodiments, the shape memory polymer is cooled from its $T_{perm}$ to a lower temperature which remains above the $T_{trans}$ and deformed, in embodiments by hand and/or mechanical means. In other embodiments, the end effector is deformed at room temperature (about 20° C. to about 25° C.) to obtain its temporary shape, although the temperature may differ depending upon the particular polymer employed. The end effector may then be cooled to a temperature below the $T_{trans}$ of the material utilized to form the end effector, at which time suture 12 is ready for use. As the $T_{trans}$ is usually greater than room temperature, in some embodiments, cooling to room temperature is sufficient to lock in the temporary shape.

There are no particular limitations on the manner in which the deformation can be achieved. Deformation can be achieved either by hand or by means of a suitable device selected to provide the desired temporary configuration to the suture and/or the end effector.

In some embodiments, to keep the shape of the suture and/or the end effector in its temporary shape, the suture should be stored at a temperature which will not cause a transition to the permanent shape. In some embodiments, the suture may be stored in a refrigerator.

In other embodiments, the shape memory polymeric materials of the present disclosure may be compressed or expanded into temporary forms that are smaller or larger in diameter than their permanent shape. As will be discussed in further detail below, in this manner, the knotted end effector may be tightened or loosened depending on the desired application.

Thus prepared, the suture and/or the end effector recovers its permanent shape upon application of energy, such as on heating, either by placement in a patient's body, or the addition of exogenous heat at a prescribed temperature, in embodiments above the $T_{trans}$ of the shape memory polymer utilized. As the suture and/or the end effector is utilized in a living body, heating with body heat (about 37° C.) is possible. In such a case, the temperature for shape programming should be as low as possible and the recovery of the permanent shape may occur fairly slowly. In embodiments, recovery of the permanent shape may occur from about 1 second to about 5 seconds after insertion into tissue.

However, in some embodiments a higher shape memory temperature may be desirable in order to make the shape recover at a slightly higher temperature than body temperature. Thus, in some cases, releasing the suture and/or the end effector from deformation to recover the permanent shape can be achieved by heating. On heating at a temperature of from about 30° C. to about 50° C., in embodiments from about 39° C. to about 43° C., the temporary shape may be released and the memorized permanent shape recovered. The higher the temperature for heating, the shorter the time for recovery of the permanent shape. The means for this heating is not limited. Heating can be accomplished by using a gas or liquid heating medium, heating devices, ultrasonic waves, electrical induction, and the like. Of course, in an application involving a living body, care must be taken to utilize a heating temperature which will not cause burns. Examples of liquid heating media include physiological saline solution, alcohol, combinations thereof, and the like.

Similarly, in other embodiments, electrically active polymers, also known as electroactive polymers, which can alter their configuration upon application of electricity, may be utilized to fashion the suture and/or the end effector. Suitable examples of electroactive polymers include poly(aniline), substituted poly(aniline)s, polycarbazoles, substituted polycarbazoles, polyindoles, poly(pyrrole)s, substituted poly(pyrrole)s, poly(thiophene)s, substituted poly(thiophene)s, poly(acetylene)s, poly(ethylene dioxythiophene)s, poly(ethylenedioxypyrrole)s, poly(p-phenylene vinylene)s, and the like, or combinations including at least one of the foregoing electroactive polymers. Blends or copolymers or composites of the foregoing electroactive polymers may also be used.

Similar to the change in shape which a shape memory material may undergo upon the application of energy, such as heat, in some embodiments, an electroactive polymer may undergo a change in shape upon the application of electricity from a low voltage electrical source (such as a battery). Suitable amounts of electricity which may be applied to effect such change will vary with the electroactive polymer utilized, but can be from about 5 volts to about 30 volts; in other embodiments, from about 10 volts to about 20 volts. The application of electricity will result in the suture and/or the end effector constructed of the electroactive polymer changing its shape.

While an electroactive polymer does not have the same permanent shape and temporary shape as those terms are described above with respect to shape memory polymers, as used herein the term "permanent shape" as applied to an electroactive polymer means the shape the electroactive polymer adopts upon the application of electricity, and the term "temporary shape" as applied to an electroactive polymer means the shape of the electroactive polymer adopts in the absence of electricity.

Filaments used for forming sutures of the present disclosure may be formed using any technique within the purview of those skilled in the art, such as, for example, extrusion, molding and/or solvent casting.

In embodiments, the suture of the present disclosure may include a yarn made of more than one filament, which may contain multiple filaments of the same or different materials.

As used herein, the terms "fibers", "filaments" and "yarns" each may be used to construct sutures, in whole or in part. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

In embodiments, sutures of the present disclosure may possess a core/sheath configuration, fibers may possess a core/sheath configuration, yarns may possess a core/sheath configuration, or both. Any material described herein, including the shape memory materials described above, may be utilized to form the core, the sheath, or both.

Sutures of the present disclosure may be monofilament or multifilament (e.g. braided). Methods for making sutures from these suitable materials are within the purview of those skilled in the art (e.g. extrusion and molding). The filaments may be combined to create a multifilament suture using any technique within the purview of one skilled in the art such as commingling, twisting, braiding, weaving, entangling, and knitting. For example, filaments may be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a nonwoven multifilament large diameter suture. In certain embodiments, a multifilament structure useful in forming a suture according to the present disclosure may be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564; the entire disclosures of each of which are incorporated by reference herein. Furthermore, the suture may include portions which are monofilament and portions which are multifilament.

Once the suture is constructed, it can be sterilized by any means within the purview of those skilled in the art.

Therapeutic agents may be utilized with sutures of the present disclosure, include end effectors. Therapeutic agents include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons ($\beta$-IFN, $\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In some embodiments, the therapeutic agent includes at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloide, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone propionate; steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the drug may be water soluble. In other embodiments, the drug may not be water soluble.

Suture 12 may be formed using any technique within the purview of those skilled in the art, such as, for example, extrusion, molding and/or gel spinning. In some embodiments, suture 12 may include a yarn made of more than one filament, which may contain multiple filaments of the same or different materials. Where suture 12 is made of multiple filaments, suture 12 may be made using any known technique such as, for example, braiding, weaving or knitting. Suture 12 may also be combined to produce a non-woven suture. Suture 12 may be drawn, oriented, crinkled, twisted, commingled or air entangled to form yarns as part of the suture forming process. In one embodiment, a multifilament suture is produced by braiding. The braiding may be done by any method within the purview of those skilled in the art.

With reference still to FIGS. 1 and 2, end effector 10 is configured to prevent complete reception of suture 12 through tissue or other material. End effector 10 forms a substantially T-shaped knot formed on distal end 12*b* of suture 12. End effector 10 defines an axis "Y" extending perpendicular to a longitudinal axis "X" of suture 12. End effector 10 includes first and second extensions 20, 30 extending perpendicularly from suture 12 in opposite directions along axis "Y" to form a T-shape. Each of first and second extension 20, 30 is formed from a plurality of throws 22*a-c*, 32*a-c*, respectively, thereby forming undulated members. As used herein, a "throw" is defined as "an at least three-hundred and sixty degree)(360° wrapping or weaving of two limbs" and "undulated" is defined as "having a wavelike or rippled form". As shown, first and second extensions 20, 30 each include three throws 22*a-c*, 32*a-c*, respectively. It is envisioned, however, that first and second extensions 20, 30 may include any number of throws 22, 32, respectively. It is further envisioned that the number of throws on first extension 20 does not need to be equal to the number of throws on second extension 30. A proximal end 12a of suture 12 may include one or more needles (not shown) and/or may include one or more barbs.

With reference to FIGS. 3A-4C, as discussed above, the suture of the present disclosure may be formed entirely, or in part, of a shape memory polymeric material. Such materials include a first or permanent configuration, and a second or temporary configuration. Transformation from the temporary configuration to the permanent configuration may result in radial expansion or contraction, axial lengthening or shortening, and/or reorientation of the suture along a length thereof.

Figure 3B:
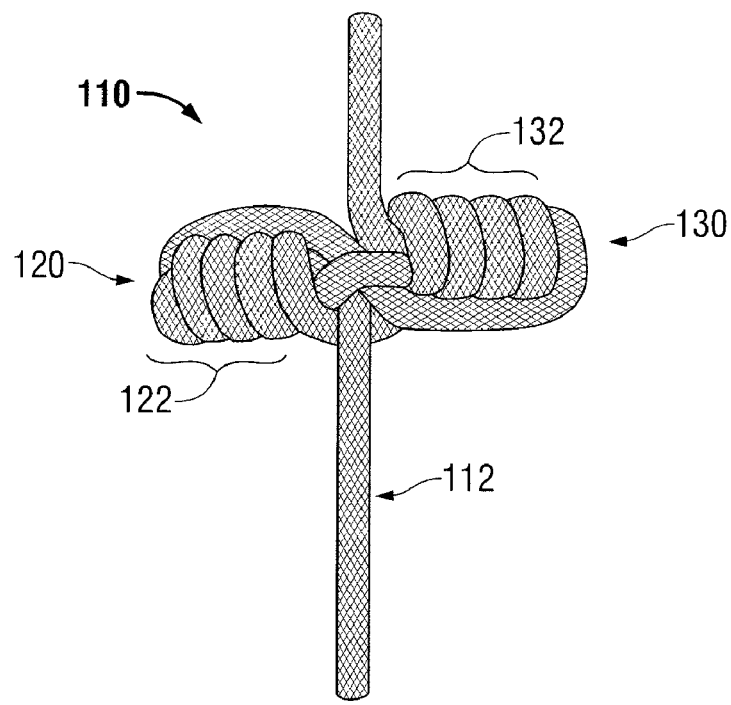

Turning now to FIGS. 3A and 3B, suture 112 is configured such that at least a portion of knotted end effector 110 is composed of a shape memory polymeric material. For example, the portions of suture 112 that corresponding to throws 122, 132 of respective extensions 120, 130 of knotted end effector 110 may be at least partially composed of shape memory polymeric material(s). When the shape memory polymeric material of suture 112 is configured to radial expand and/or axially shorten along a length thereof, knotted end effector 110 may be tied loosely to permit movement of extensions 120, 130. During the transition from the temporary configuration (FIG. 3A) to the permanent configuration (FIG. 3B), knotted end effector 110 will tighten about itself, thereby creating a more rigid or secure knot. Alternatively, when the shape memory polymeric material forming suture 112 is configured to radial contract and/or axially lengthen along a length thereof, knotted end effector 110 may loosen, thereby creating a more slack or pliable knot that may be more easily directed through tissue.

Figure 4:
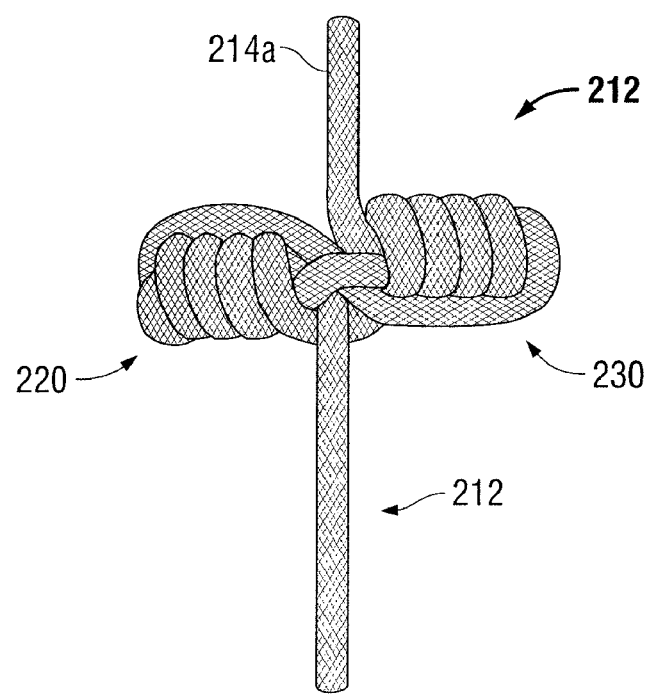
FIG. 4 is a front view of another embodiment of the present disclosure in a first configuration.
Figure 4A:
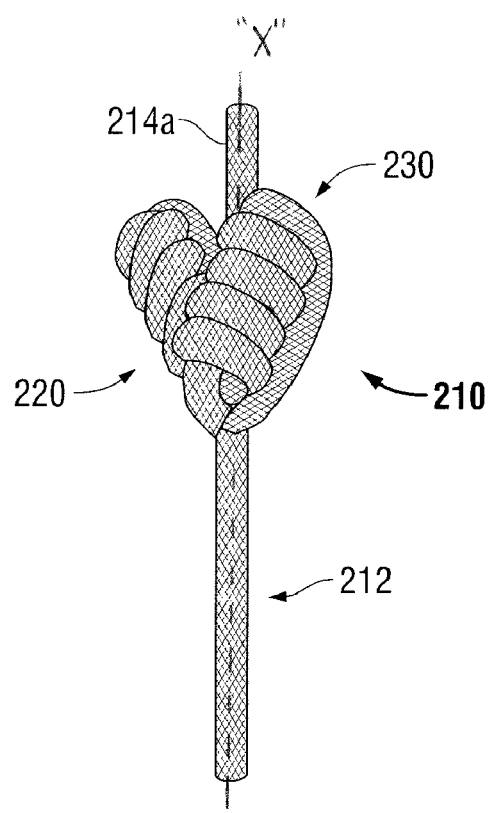
FIGS. 4A-4C are front views of the suture of FIG. 4 in alternate second configurations.
Figure 4B:
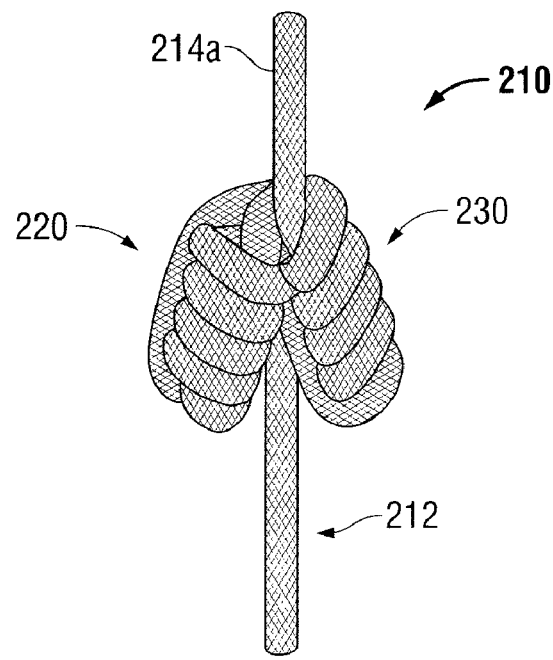
Figure 4C:
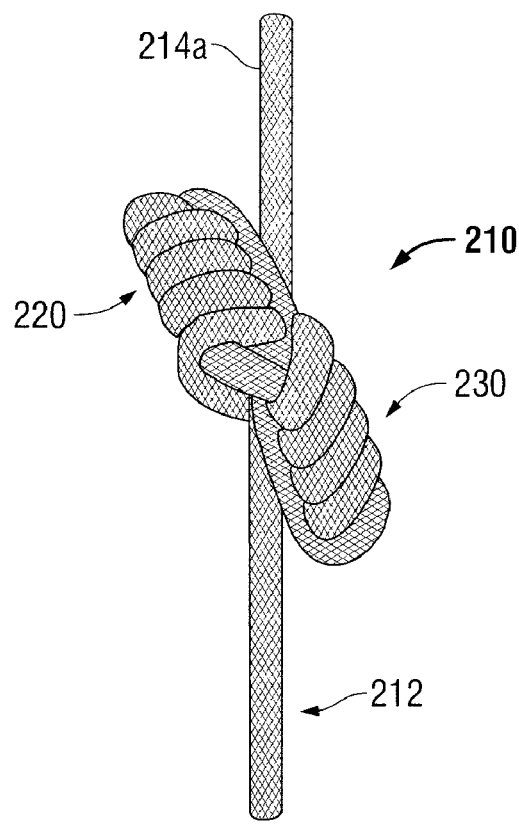

With reference now to FIGS. 4-4C, suture 212 may be configured to include portions of shape memory polymeric materials positioned such that extensions 220, 230 of knotted end effector 210 are flexible and/or are arranged substantially parallel to longitudinal axis "x", i.e., such that knotted end effector 210 assumes a substantially "Y" shape (FIG. 4A) when the shape memory portions are in the temporary configuration, and upon transitioning to the permanent configuration, end effector 210 assumes a substantial "T" shape (FIG. 4). In alternative embodiments, knotted end effector 210 may assume a substantially inverted "Y" shape (FIG. 4B), a shape including one extension directed proximally and the other extension directed distally (FIG. 4C), or instead, extensions 220, 230 may be flexibly disposed on distal end 214a of suture 212 to move freely as directed. In this manner, when the shape memory portions of suture 212 are in the temporary configuration (FIG. 4A, 4B, 4C), knotted end effector 210 can be more easily received through tissue and, upon transitioning from the temporary configuration to the permanent configuration, knotted end effector 210 becomes locked within the tissue, thereby limiting movement of end effector 210 through tissue. Alternatively, suture 212 is configured such that end effector 210 assumes a substantial "T" shape in the temporary configuration, and upon transitioning to the permanent configuration, extensions 220, 230 of knotted end effector 210 become slack or orient themselves substantially along the longitudinal axis "x" in the substantially "Y" shape (FIG. 4A), in the substantially inverted "Y" shape (FIG. 4B), with one extension directed distally and the other extension directed proximally (FIG. 4C) or with extensions 220, 230 flexibly disposed on distal end 214a of suture 212. In this manner, suture 212 is configured to be more easily pulled through tissue once knotted end effector 210 has transitioned from the temporary configuration to the permanent configuration.

Figure 5:
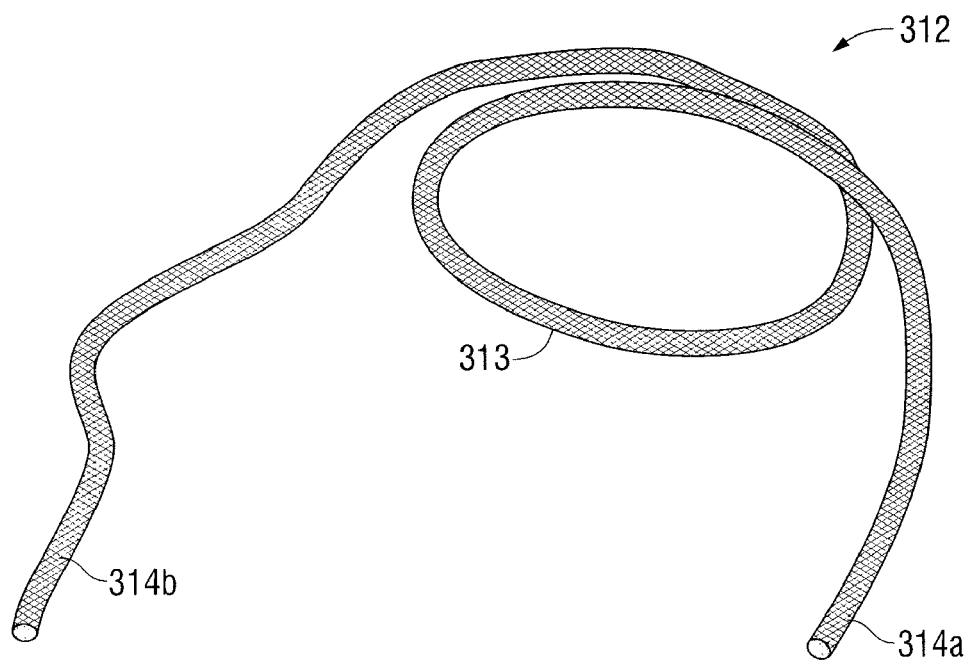
FIGS. 5-17 show sequential steps of a method of forming the end effector of FIGS. 1 and 2.

The method of forming an end effector 310 will now be described with reference to FIGS. 5-17. Referring initially to FIG. 5, suture 312 is cut to a desired length. The length of the suture may vary depending on the application for which suture 312 is being used. The size of end effector 310 may also affects the length of suture 312. The more throws 322, 332 (FIG. 8) formed in respective extension 320, 330 of end effector 310, the greater the length or size required of suture 312. The thickness of suture 312 also affects length of suture 312. Alternatively, suture 312 may be formed on the free end of a spool of thread (not shown) and cut to length following the forming of end effector 310. A first, short end 314a of suture 312 is then crossed over a second, long end 314b of suture 312 to form a first loop 313. First loop 313 should be of sufficient size to permit wrapping of first end 314a through first loop 313 multiple times. Although "short" and "long" are used to refer to first and second ends 314a, 314b, respectively, in some embodiments, short end 314a may actually be of equal or longer length than long end 314b.

Figure 6:
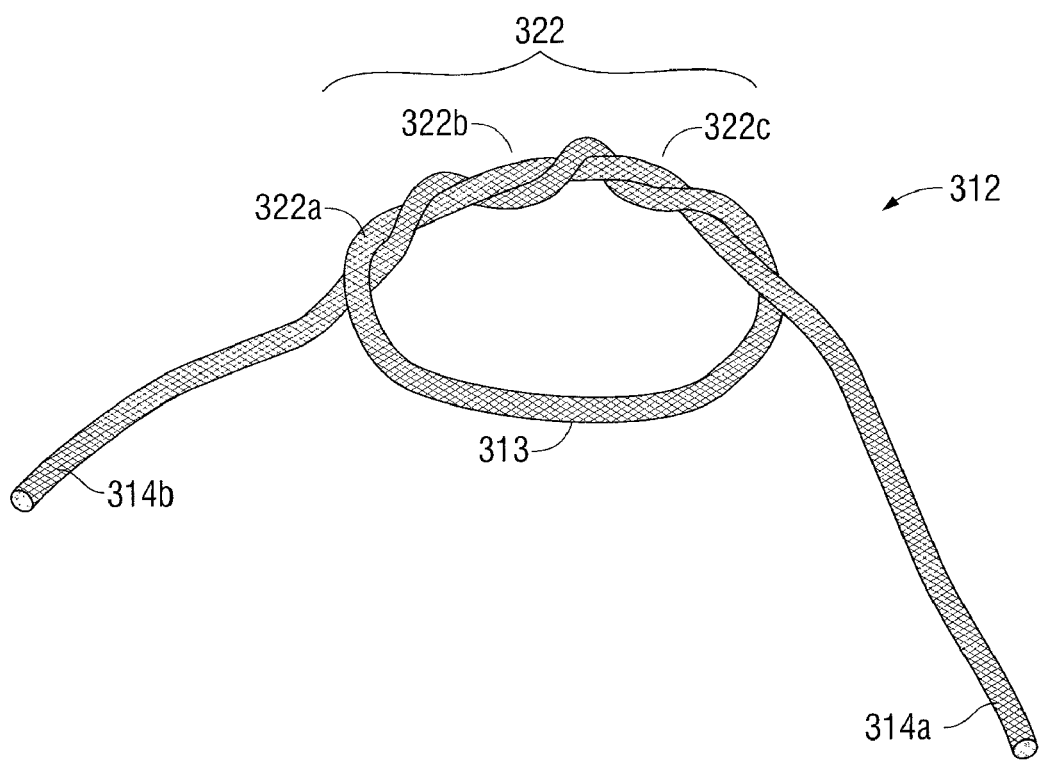

Turning to FIG. 6, first end 314a of suture 312 is then wrapped around suture 312 within loop 313 "n" number of times to form "n" number of throws 322. As shown, first end 314a is wrapped around suture 312 (3) three times to form three (3) throws 322a-c. As discussed above, first end 3114a of suture 312 may be wrapped around suture 312 within loop 313 more or less than three (3) times.

Figure 7:
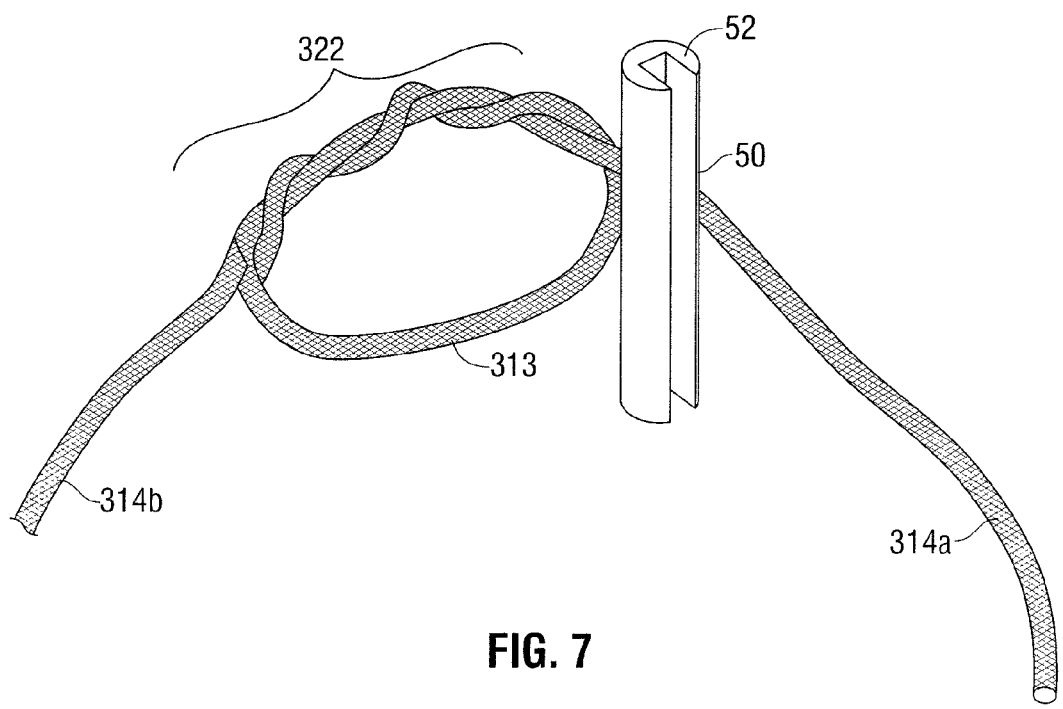

With reference now to FIG. 7, first loop 313 is next placed adjacent to a fixture 50, with fixture 50 being received in the V-shaped notch between first loop 313 and first end 314a. As will be discussed in further detail below, fixture 50 includes a channel 52 extending along a length thereof.

Figure 8:
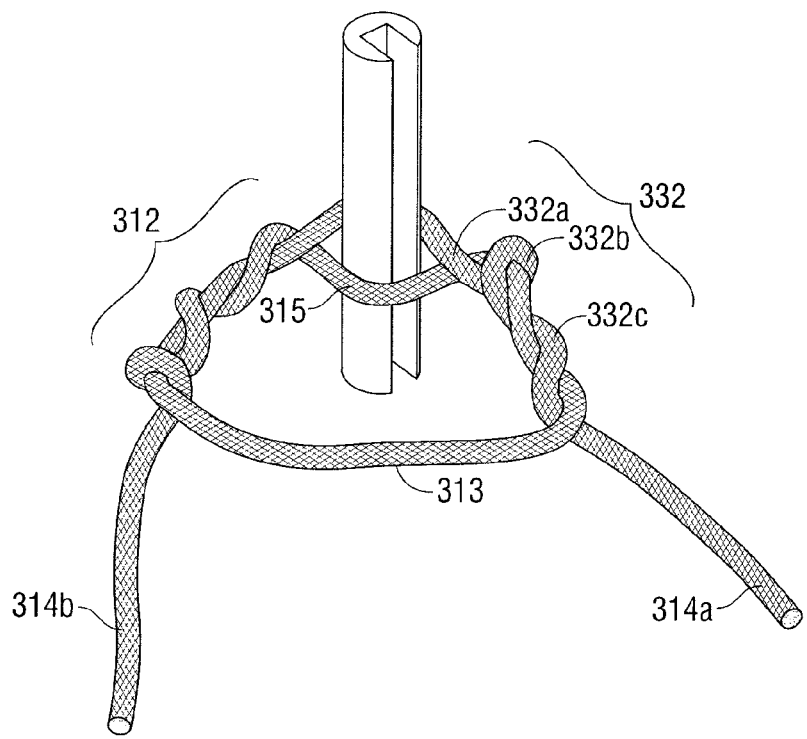

Turning to FIG. 8, first end 314a of suture 312 is next wrapped around fixture 50 to form a second loop 315. First end 314a is then wrapped around suture 312 within loop 313 "m" number of times to form "m" number of throws 332. As shown, first end 314a is wrapped around suture 312 three (3) times to form three (3) throws 332a-c. As discussed above, first end 314a may be wrapped around suture 312 more or less than three (3) times and does not need to be equal to "n" number of throws 322 formed on the opposite side of first loop 313.

Figure 9:
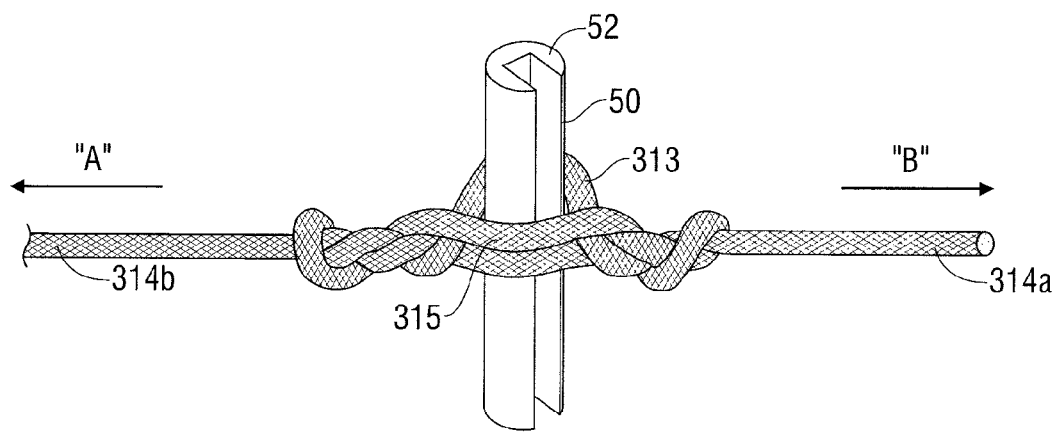
Figure 10:
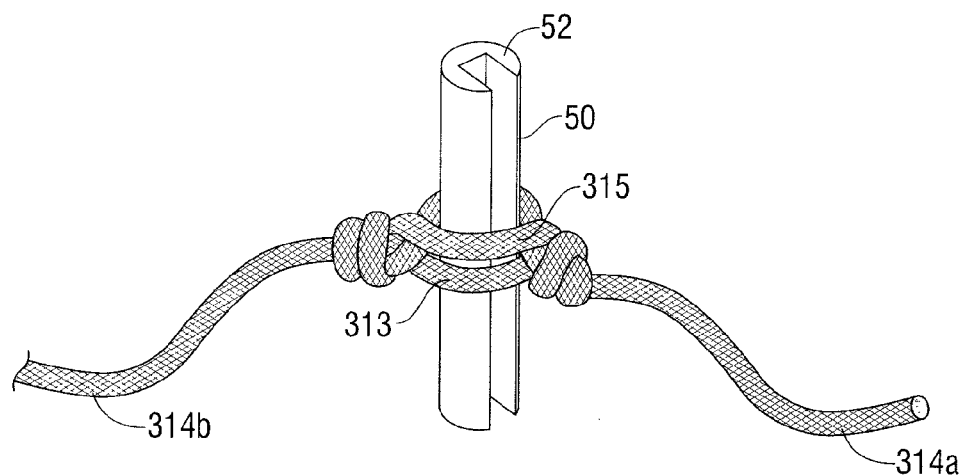

With reference now to FIGS. 9 and 10, first and second ends 314a, 314b of suture 312 are next pulled in opposing directions, as indicated by arrows "A" and "B" (FIG. 9), thereby tightening first and second loops 313, 315 about fixture 50 (FIG. 10).

Figure 11:
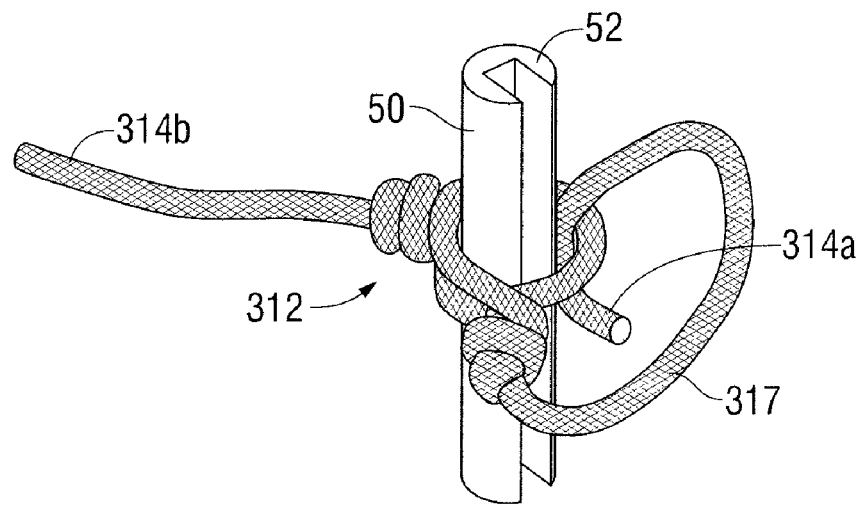

As noted above, fixture 50 includes a channel 52 formed along a length thereof to permit the passage of suture ends 314a, 314b through second loop 315. With reference now to FIG. 11, first end 314a of suture 312 is threaded through second loop 315 by passing first end 314a through channel 52 of fixture 50. It is envisioned, however, that the threading of first end 314a through second loop 315 may accomplished without the use and/or presence of channel 52. First end 314a is threaded through second loop 315 from the top, as shown, to form a third loop 317. In an alternative embodiment, first end 314a of suture 312 may be threaded through second loop 315 from the bottom.

Figure 12:
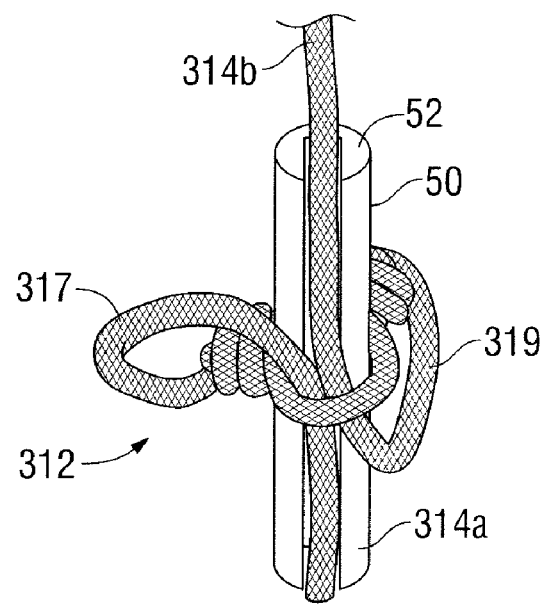

Referring now to FIG. 12, second end 314b of suture 312 is next threaded through second loop 315, through channel 52, if present, in a direction opposite to that which first end 314a was threaded. As shown, second end 314b of suture 312 is threaded through second loop 315 from the bottom up to form a fourth loop 319. In another embodiment, second end 314b may be fed through second loop 315 in the same direction that first end 314a was threaded through second loop 315. In this manner, second end 314b is threaded through second loop 315 from the top down. The direction from which short and long ends 314a, 314b are threaded through second loop 315 determines the final configuration of end effector 310. In yet another embodiment, second end 314b may be threaded through second loop 315 from the top down or the bottom up, and short end 314b may be severed adjacent to outer throw 332c without short end 312 being threading through second loop 315.

Figure 13:
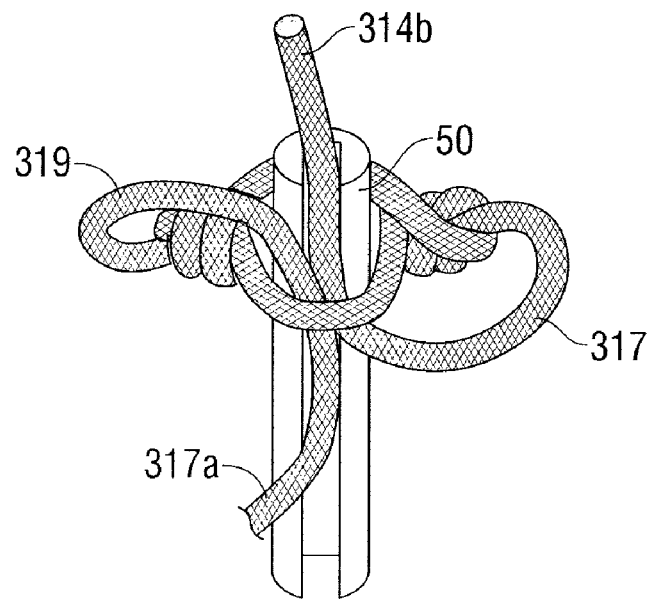
Figure 14:
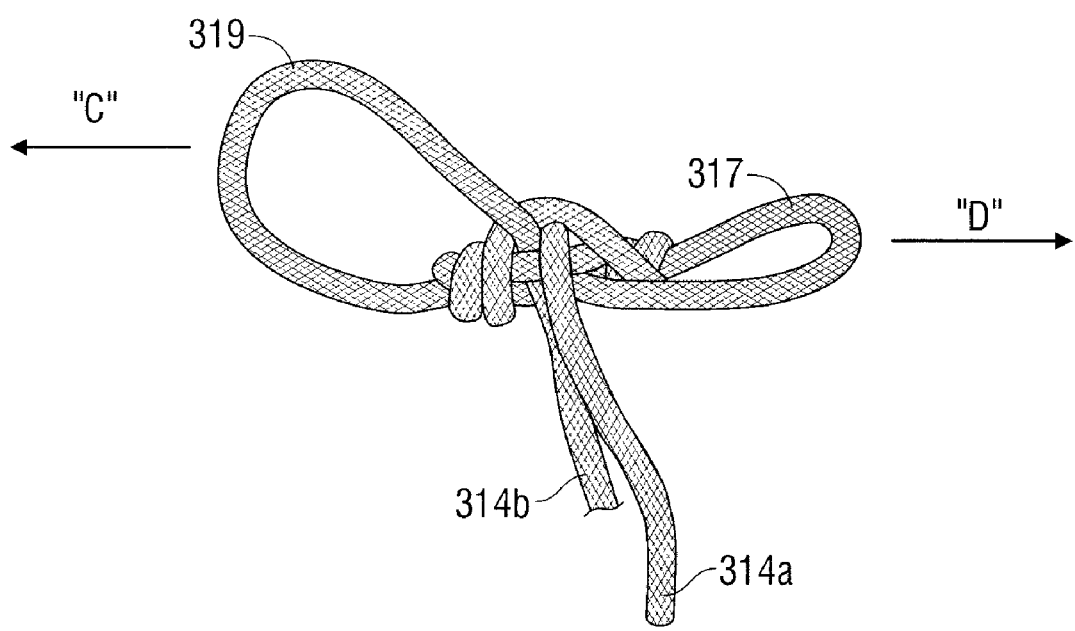

With reference to FIGS. 13 and 14, suture 112 is next removed from fixture 50 (FIG. 10) and third and fourth loops 317, 319 are then pulled in opposite directions (FIG. 11) along an axis perpendicular to the longitudinal axis of suture 312, as indicated by arrows "C" and "D", to tighten first and second loops 313, 315 about short and long ends 314a, 314b.

Figure 15:
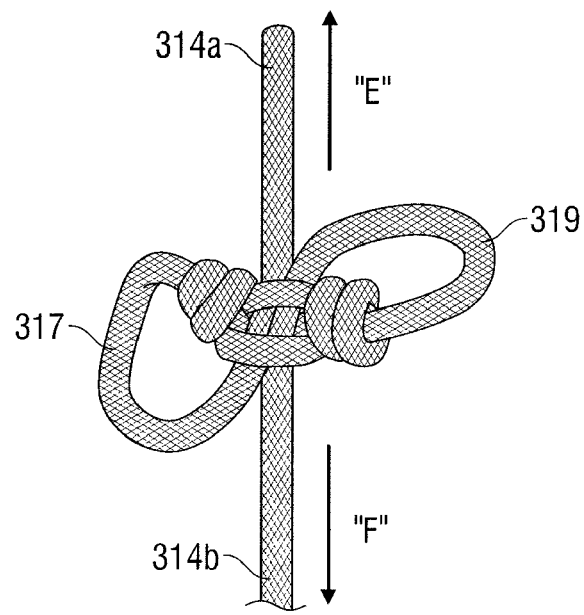

Turning now to FIG. 15, next short and long ends 114a, 114b are pulled in opposite directions, as indicated by arrows "E" and "F," to tighten third and fourth loops 317, 319 about respective throws 322a-c, 132a-c.

Figure 16:
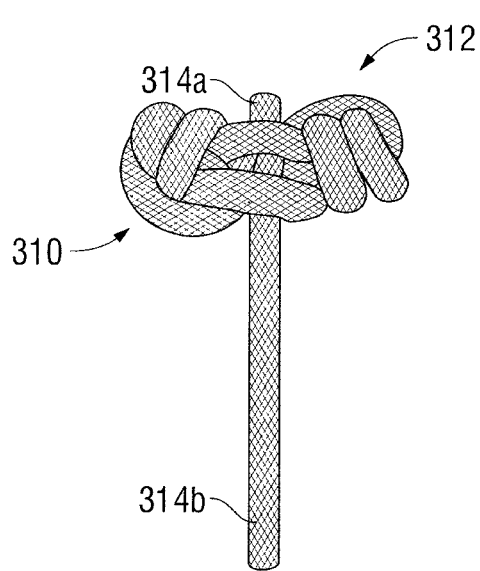
Figure 17:
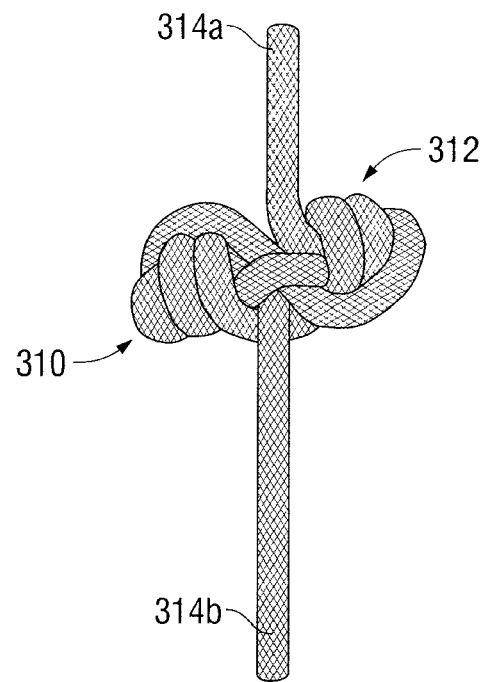

With reference now to FIGS. 16 and 17, first end 314a may then be cut as close to or as far from end effector 310 as desired. In an alternative embodiment, first end 314a may be left uncut, thereby providing a clinician with a means for retracting suture 312.

Figure 18:
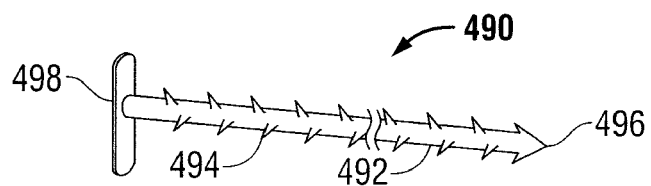
FIG. 18 is a perspective view of an alternate embodiment of a suture according to the present disclosure.
Figure 18A:
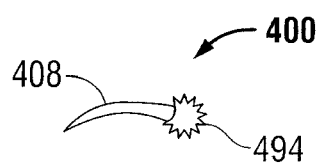
FIGS. 18A-18S are perspective views of various embodiments of alternate end effectors capable of benefiting from the aspects of the present disclosure.
Figure 18B:
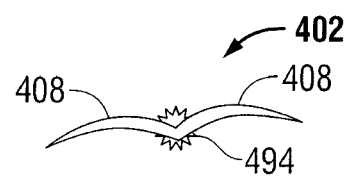
Figure 18C:
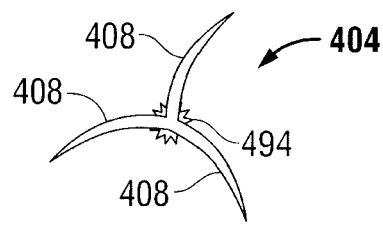
Figure 18D:
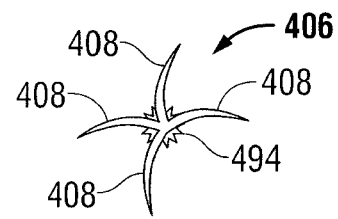
Figure 18E:
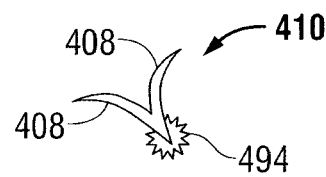
Figure 18F:
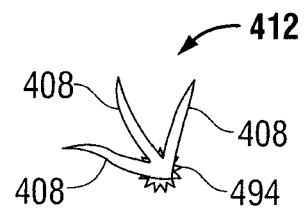
Figure 18G:
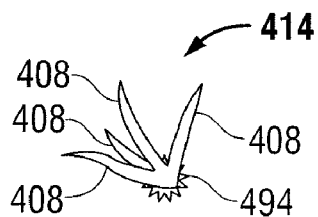
Figure 18H:
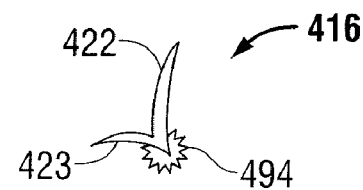
Figure 18I:
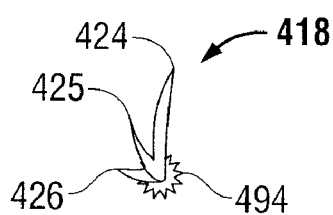
Figure 18J:
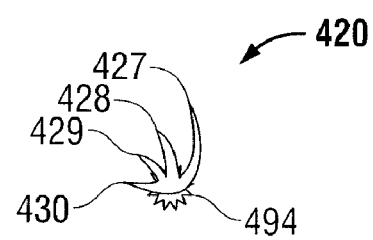

Alternate end effectors that may benefit form the aspects of the present disclosure are included in U.S. Patent Publication No. 2005/0267531 to Ruff et al., the entire disclosure of which is incorporated by reference herein. Referring initially to FIG. 18, in one embodiment a single-directional barbed suture 490 includes a suture body 492 with barbs 494 extending from around the periphery thereof, a pointed end 496, and an end effector 498 on the opposite end. Anchor 498 includes a bar which extends radially outwardly of the suture body 492 in a plane substantially perpendicular to the longitudinal axis of suture body 492. This configuration generally gives barbed suture 490 a "T" shape. With reference to FIGS. 18A-18S, end effector 498 may include other shapes and configurations. Each of the end effectors shown in FIGS. 18A-18L have limbs which extend radially outwardly from the suture body 492 a greater distance than the barbs 494. End effectors 498 on the barbed sutures 400, 402, 404, 406 depicted in FIGS. 18A-18D, respectively, have one or a plurality of limbs 408 generally evenly spaced around the periphery at the end of the suture. The embodiments of the barbed sutures 410, 412, 414 shown in FIGS. 18E-18G have end effector 498 including a plurality of limbs 408 which extend from only a portion of the periphery at the end of the suture body 492. FIGS. 18H-18J show embodiments of the barbed sutures 416, 418, 420 wherein each of the respective limbs 422-423, 424-426, 427-430 are of different lengths.

Figure 18K:
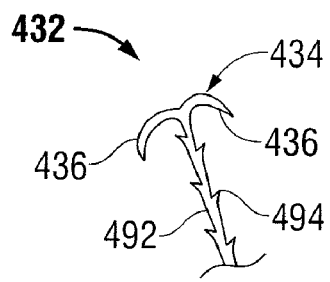
Figure 18L:
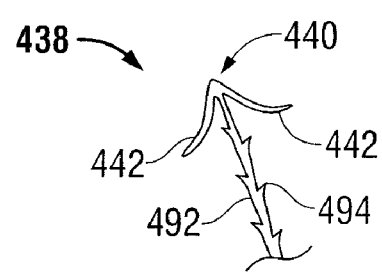
Figure 18M:
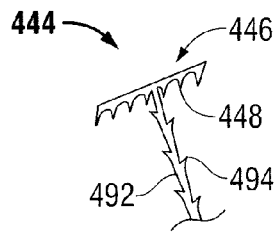
Figure 18N:
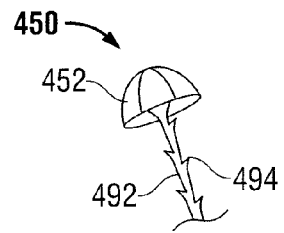
Figure 18O:
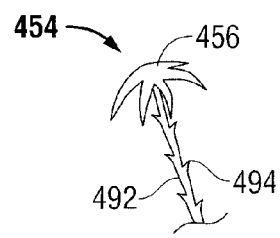
Figure 18P:
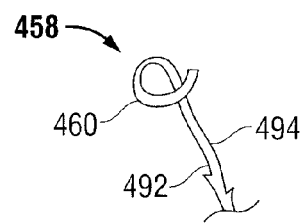
Figure 18Q:
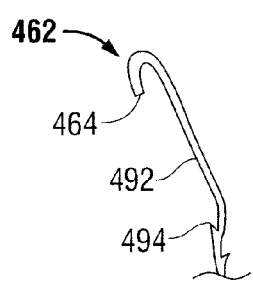
Figure 18R:
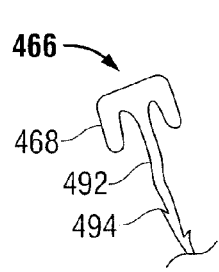
Figure 18S:
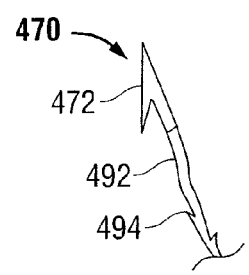

FIGS. 18K-18S are further embodiments of barbed sutures at one end. FIG. 18K shows a barbed suture 432 that has an end effector 434 having limbs 436 that are concave toward the other end of the suture. FIG. 18L shows a barbed suture 438 with an end effector 440 having limbs 442 that are concave away from the pointed end of the suture. FIG. 18M shows a barbed suture 444 with an anchor 446 as shown in FIG. 18, further including a plurality of segments 448 extending from the bar toward the other end of the suture. FIG. 18N shows a barbed suture 450 having a hemispherical end effector 452. FIG. 18O shows a barbed suture 454 having an end effector 456 that resembles a coneflower. FIG. 18P shows a barbed suture 458 having an end effector 460 formed by a loop of the body 492 that crosses itself to form a clip, wherein tissue may be received between the clip. FIG. 18Q shows a barbed suture 462 having an end effector 464 formed by a hook of the suture body 492. FIG. 18R shows a barbed suture 466 having an end effector resembling an "M" wherein body 492 of the suture extends from the middle leg of the "M". FIG. 18S shows a barbed suture 470 having a single barb 472, larger than opposing barbs 494, extending towards the other end of suture 470. As demonstrated by the variety of end effector designs of FIGS. 18-18S, many anchor designs are possible for use with the barbed suture and within the scope of the present invention. As previously described, in a temporary shape, the end effectors may be positioned substantially parallel to the elongate body. When the end effectors are in the permanent shape, as illustrated in FIGS. 18-18S, the end effectors prevent movement of the distal portion of the suture thru tissue.

The end effectors shown in FIGS. 18-18S may be integrally formed with body 492 of the barbed suture or, alternatively, may be mounted to the end of the suture.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that any of the above described sutures may include a loop formed on a distal of the end effector to permit withdrawal of the suture from within tissue.

What is claimed is:

1. A suture comprising:
a body portion defining a longitudinal axis; and
an end effector formed from the body portion, the end effector comprising a shape memory polymeric material and including first and second extensions, each of the first and second extensions being formed of a plurality of throws, wherein the first and second extensions extend outwardly from the longitudinal axis in opposite directions when the end effector is in a permanent configuration and the first and second extensions extend substantially along the longitudinal axis when the end effector is in a temporary position.

2. The suture of claim 1, wherein the end effector is integrally formed with the body portion.

3. The suture of claim 1, wherein the end effector is substantially perpendicular to the longitudinal axis when in the permanent configuration.

4. The suture of claim 1, wherein the end effector defines a substantially T-shape when the end effector is in the permanent configuration.

5. The suture of claim 1, wherein the end effector is substantially parallel to the longitudinal axis when the end effector is in the temporary configuration.

6. The suture of claim 1, wherein the end effector defines a substantially Y-shape when the end effector is in the temporary configuration.

7. The suture of claim 1, wherein the shape memory polymeric material is selected from the group consisting of degradable materials, non-degradable materials, and combinations thereof.

8. The suture of claim 1, wherein the shape memory polymeric material comprises a non-degradable material selected from the group consisting of polyolefins, polyethylene glycols, polyethylene oxides, polyolefin copolymers, fluorinated polyolefins, polyamides, polyamines, polyimines, polyesters, polyethers, polybutesters, polyurethanes, acrylic polymers, methacrylics polymers, vinyl halide polymers and copolymers, polyvinyl alcohols, polyvinyl ethers, polyvinylidene halides, polychlorofluoroethylene, polyacrylonitrile, polyaryletherketones, polyvinyl ketones, polyvinyl aromatics, polyvinyl esters, copolymers of vinyl monomers, acrylonitrile-styrene copolymers, ABS resins, ethylene-vinyl acetate copolymers, alkyd resins, polycarbonates, polyoxymethylenes, polyphosphazines, polyimides, epoxy resins, aramids, rayons, spandex, silicones, and combinations thereof.

9. The suture of claim 1, wherein the shape memory polymeric material comprises a bioabsorbable material selected from the group consisting of aliphatic polyesters, polyamides, polyamines, polyalkylene oxalates, poly(anhydrides), polyamidoesters, copoly(ether-esters), poly(carbonates), poly(hydroxyalkanoates), polyimide carbonates, poly(imino carbonates), polyorthoesters, polyoxaesters, polyphosphazenes, poly(propylene fumarates), polyurethanes, polymer drugs, biologically modified bioabsorbable polymers, and copolymers, homopolymers, and combinations thereof.

10. The suture of claim 9, wherein the shape memory polymeric material comprises an aliphatic polyester selected from the group consisting of homopolymers and copolymers of lactide, glycolide, epsilon-caprolactone, p-dioxanone, trimethylene carbonate, alkyl derivatives of trimethylene carbonate, Δ-valerolactone, β-butyrolactone, γ-butyrolactone, ε-decalactone, hydroxybutyrate, hydroxyvalerate, 1,4-dioxepan-2-one, 1,5-dioxepan-2-one, 6,6-dimethyl-1,4-dioxan-2-one, 2,5-diketomorpholine, pivalolactone, α,α diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and combinations thereof.

11. The suture of claim 1, wherein the shape memory polymeric material comprises a biodegradable polymer selected from the group consisting of poly(amino acids), collagen, elastin, fibrin, fibrinogen, silk, albumin, peptides including sequences for laminin and fibronectin, hyaluronic acid, dextran, alginate, chitin, chitosan, cellulose, glycosaminoglycan, gut, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, nitrocelluloses, chitosan, and combinations thereof.

12. The suture of claim 1, wherein the shape memory polymeric material comprises a polymer selected from the group consisting of oligo (epsilon-caprolactone) dimethacrylates, oligo (epsilon-caprolactone) butyl acrylates, (n-butyl acrylate), oligo (epsilon caprolactone)diol/oligo (p-dioxanone)diol copolymers, polycaprolactone dimethacrylate poly(butyl acrylate) blends, and combinations thereof.

13. The suture of claim 1, wherein the shape memory polymeric material comprises a block copolymer of polydioxanone and polylactide.

14. The suture of claim 13, wherein the polydioxanone is present in an amount from about 15 mol % to about 20 mol % of the copolymer and the polylactide is present in an amount from about 80 mol % to about 85 mol % of the copolymer.

15. The suture of claim 1, wherein the shape memory polymeric material comprises a block copolymer of trimethylene carbonate and polylactide.

16. The suture of claim 15, wherein the trimethylene carbonate is present in an amount from about 15 mol % to about 20 mol % of the copolymer and the polylactide is present in an amount from about 80 mol % to about 85 mol % of the copolymer.

17. The suture of claim 1, wherein each of the plurality of throws defines a central axis that is perpendicular to the longitudinal axis when the end effector is in a permanent configuration.

18. The suture of claim 1, wherein the first and second extensions are fixedly disposed relative to the longitudinal axis.

19. The suture of claim 1, wherein the plurality of throws of each of the first and second extensions are parallel.

20. The suture of claim 1, wherein the plurality of throws of each of the first and second extensions abut one another.

21. A suture comprising:
a body portion defining a longitudinal axis; and
an end effector integrally formed from the body portion, the end effector comprising a shape memory polymeric material and including first and second extensions, each of the first and second extensions being formed of a plurality of throws, wherein the first and second extensions extend substantially along the longitudinal axis when the end effector is in a permanent configuration and the first and second extensions extend outwardly from the longitudinal axis in opposite directions when the end effector is in a temporary configuration.

22. The suture of claim 21, wherein the end effector is substantially perpendicular to the longitudinal axis when in the temporary configuration.

23. The suture of claim 21, wherein the end effector defines a substantially T-shape when the end effector is in the temporary configuration.

24. The suture of claim 21, wherein the end effector is substantially parallel to the longitudinal axis when the end effector is in the permanent configuration.

25. The suture of claim 21, wherein the end effector defines a substantially Y-shape when the end effector is in the permanent configuration.

26. A suture comprising:
a body portion defining a longitudinal axis; and
an end effector comprising a shape memory polymeric material integrally formed from the body portion, the end effector including first and second extensions extending outwardly from the longitudinal axis, each of the first and second extensions being formed of a plurality of throws; wherein either or both of the first and second extensions radially expands with respect to the longitudinal axis as the shape memory material transitions the end effector from a temporary configuration to a permanent configuration.

27. A suture comprising:
a body portion defining a longitudinal axis; and
an end effector comprising a shape memory polymeric material integrally formed from the body portion, the end effector including first and second extensions extending outwardly from the longitudinal axis, each of the first and second extensions being formed of a plurality of throws; wherein either or both of the first and second extensions radially contracts with respect to the longitudinal axis as the shape memory material transitions the end effector from a permanent configuration to a temporary configuration.

* * * * *